(12) United States Patent
Wu et al.

(10) Patent No.: US 8,436,996 B2
(45) Date of Patent: May 7, 2013

(54) APPARATUS AND METHOD FOR ENHANCING THE ELECTROMAGNETIC SIGNAL OF A SAMPLE

(76) Inventors: Wen-Li Wu, Gaithersburg, MD (US); Shuhul Kang, Gaithersburg, MD (US)

( * ) Notice: Subject to any disclaimer, the term of this patent is extended or adjusted under 35 U.S.C. 154(b) by 204 days.

(21) Appl. No.: 12/787,702

(22) Filed: May 26, 2010

(65) Prior Publication Data

US 2010/0315627 A1 Dec. 16, 2010

Related U.S. Application Data

(60) Provisional application No. 61/187,484, filed on Jun. 16, 2009.

(51) Int. Cl.
*G01J 4/00* (2006.01)

(52) U.S. Cl.
USPC .......................................................... 356/369

(58) Field of Classification Search ........... 356/364–369
See application file for complete search history.

(56) References Cited

U.S. PATENT DOCUMENTS

| | | | | |
|---|---|---|---|---|
| 4,733,926 | A * | 3/1988 | Title | 359/352 |
| 5,394,245 | A * | 2/1995 | Sato | 356/369 |
| 5,838,448 | A * | 11/1998 | Aiyer et al. | 356/632 |
| 6,392,756 | B1 * | 5/2002 | Li et al. | 356/632 |
| 6,563,578 | B2 * | 5/2003 | Halliyal et al. | 356/237.4 |
| 7,283,234 | B1 * | 10/2007 | Woollam et al. | 356/369 |
| 2001/0013935 | A1 | 8/2001 | Watanabe et al. | |
| 2002/0048019 | A1 * | 4/2002 | Sui et al. | 356/369 |

OTHER PUBLICATIONS

Othman, M.T., et at., Characterization of porous low-k films using variable angle spectroscopic ellipsometry, J. Appl. Phys. 99, 083503 (2006).*

C.M. Herzinger et al., Ellipsometric determination of optical constants . . . , Journal of Applied Physics, vol. 83, No. 6. Mar 15, 1998, pp. 3323-3336.

G.A. Candela et al., Preparation and Certification of SRM-2530 . . . , NIST Special Publication 260-109, Issued Oct. 1988, pp. coverpage, I,. & 1-37.

* cited by examiner

*Primary Examiner* — Gregory J Toatley
*Assistant Examiner* — Dominic J Bologna

(57) ABSTRACT

The present invention is an apparatus and method for enhancing the electromagnetic signal of a sample for ellipsometry which uses at least one auxiliary layer and at least one substrate layer.

24 Claims, 5 Drawing Sheets

APPARATUS AND METHOD FOR ENHANCING THE ELECTROMAGNETIC SIGNAL OF A SAMPLE

CROSS-REFERENCE TO RELATED APPLICATIONS

This application claims priority to U.S. Provisional Application No. 61/187,484 filed on Jun. 16, 2009.

STATEMENT REGARDING FEDERALLY SPONSORED RESEARCH OR DEVELOPMENT

This invention (NIST Case #09-013) was developed with funds from the National Institute of Standards and Technology.

FIELD OF INVENTION

The present invention relates to the field of ellipsometry, and more particularly to an apparatus and method for enhancing the electromagnetic signal of a sample for ellipsometry.

TERMS OF ART

Figure 1A:
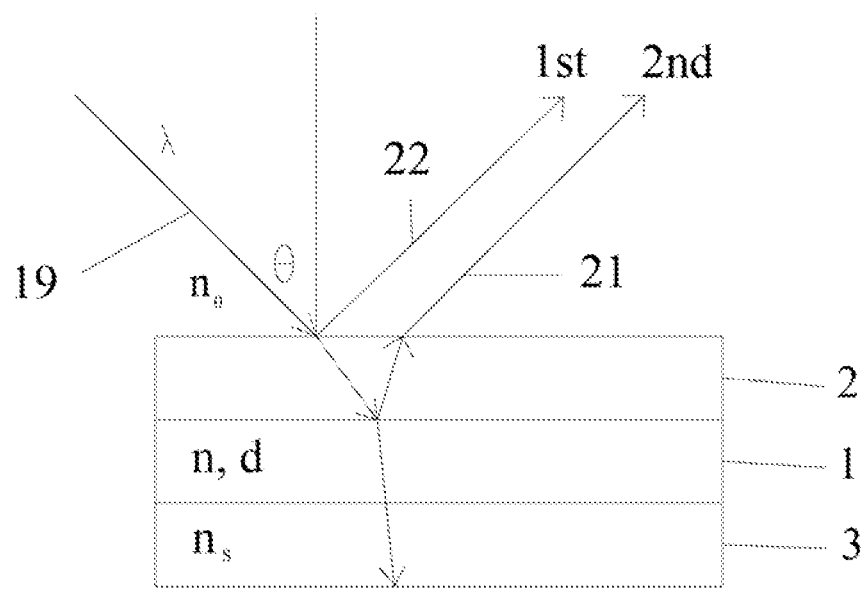
FIG. 1A illustrates an exemplary embodiment of an apparatus for enhancing the electromagnetic signal of a sample, which is placed between a light source and an auxiliary layer.

As used herein, the term "substrate" refers to a layer capable of supporting an auxiliary layer, sample, functional layer or any other material. A substrate may be comprised of silicon or gold or functionally equivalent materials.

As used herein, the term "auxiliary layer" refers to a layer having a specific thickness(es) and optical constant so that either alone or in combination with other auxilarly layers produces deconstructive interference about s-polarization to minimize reflectivity of the component with s-polarization. Examples of materials which may be used for auxiliary layers include, but are not limited to, silicon oxide, aluminum oxide and functional equivalents thereof.

As used herein, term "functional layer" refers to a layer that may act as a protective or absorptive layer between a substrate, auxiliary layer, and/or sample or may hold a sample in place to permit analysis. Examples of functional layers include, but are not limited to, silanes to facilitate organic polymer absorption, or functional equivalents thereof.

As used herein, the term "piping" refers to any structure used to a carry a liquid or gas.

As used herein, the term "means to attach piping" refers to the use of clamps, welding, adhesion or any other process known in the art for attaching one structure to another.

As used herein, the term "thickness" refers to a dimension, which is mathematically defined or determined by trial and error.

As used herein, the term "chromatography component" refers to an instrument or laboratory technique used to separate the components of sample. Examples of chromatography components include, but are not limited to, HPLC, GLC, column chromatography, TLC, ion exchange chromatography, affinity chromatography, size exclusion chromatography, reverse phase chromatography, combinations of the foregoing and functional equivalents.

BACKGROUND

Spectroscopic ellipsometry and reflective spectroscopy are powerful tools in the characterization of materials at interfaces that are used in technologies such as nanotechnology, biotechnology, and photocell fabrication. Silicon or other wafers with no coating have been used extensively as the substrate for ellipsometry and IR spectroscopy and oxide coated wafers already exist in market, but using the wafers with specific oxide thicknesses to achieve optimal or near optimal signals for ellipsometry and IR spectroscopy for a specific specimen type, does not exist. This invention relates to the application of non-absorptive auxiliary layers (coatings) with specific thicknesses and optical constant, to a wafer or a substrate (collectively referred to as the substrate layer) to amplify the reflective signal at a given wavelength of interest.

SUMMARY OF THE INVENTION

The present invention is an apparatus and method for enhancing the electromagnetic signal of a sample for ellipsometry comprised of at least one substrate layer and at least one auxiliary layer bound to the at least one substrate layer. The auxiliary layer has a thickness and refractive index which produces deconstructive interference about s-polarization reducing the reflectively of the component with s-polarization.

DETAILED DESCRIPTION OF INVENTION

For the purpose of promoting an understanding of the present invention, references are made in the text to exemplary embodiments of an apparatus for enhancing the electromagnetic signal of a sample for ellipsometry, only some of which are described herein. It should be understood that no limitations on the scope of the invention are intended by describing these exemplary embodiments. One of ordinary skill in the art will readily appreciate that alternate but functionally equivalent substrates and thicknesses may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change in the basic function to which it is related.

FIG. 1A illustrates an exemplary embodiment of a first major configuration, which has incident light directed at sample 2, which is layered on top of auxiliary layer 1. Auxiliary layer 1 is placed on top of substrate layer 3. This configuration of a coating or coatings (i.e., auxiliary layers) works optimally when refractive index "n", thickness "d" and incident angle "θ" of the light source comport with the following equation set 1:

$$d = \frac{\lambda}{\sqrt[4]{n^2 - n_0^2 \sin^2 \theta}}$$

$$\theta = \tan^{-1} \frac{\sqrt{n_0^2 n_s^2 - n^4}}{n^2 - n_0^2}$$

$$n \leq \sqrt{n_0 n_s}$$

Figure 1B:
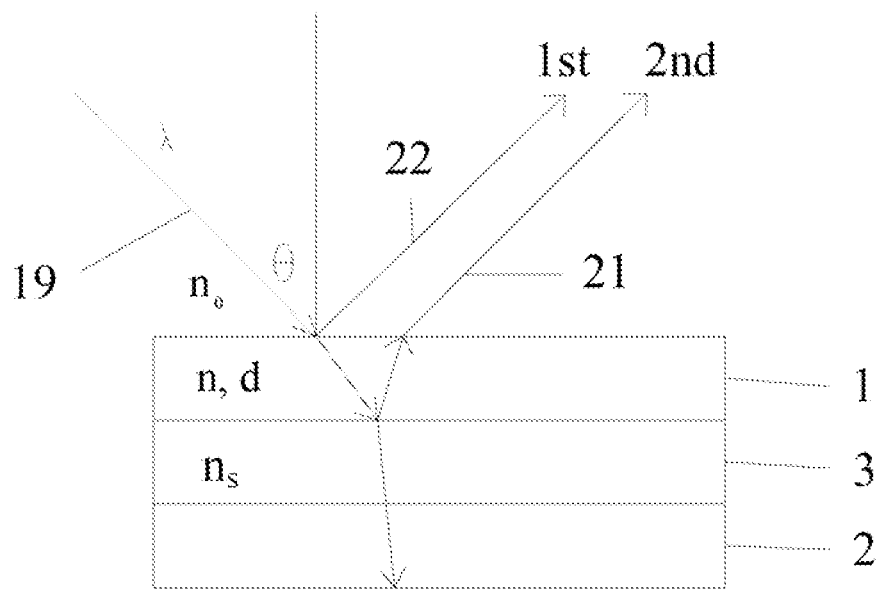
FIG. 1B illustrates an exemplary embodiment of an apparatus for enhancing the electromagnetic signal of a sample, which is placed behind a light source, an auxiliary layer, and a substrate layer.

FIG. 1B illustrates an exemplary embodiment of a second major configuration which has incident light directed at auxiliary layer 1, which is layered on top of substrate layer 3. Sample 2 is placed behind substrate layer 3. This configuration of a coating or coatings (i.e., auxiliary layers) is optimal when thickness "d" (auxiliary layer), optimal incident angle "θ" of the light source, and the optimal refractive index "$n_{op}$" comport with the following equation set 2:

$$d = \frac{\lambda}{\sqrt{A(n-1) + B(n-1)^2}}$$

Where $A = 37.26(n_s - 1.682)^{-1/8}$ and $B = 14.587(n_s - 2.171)^{1/6.5}$ $$\theta = \tan^{-1}\left(\frac{1}{C(n-1) + D(n-1)^2}\right)$$

Where $C = (-0.262 + 0.454 n_s)^{-1}$ and $D = -(1.181 - 0.112 n_s)^4$ $$n_{op} = .85 + 0.189 n_s$$

For all the above equations, the refractive indexes "n" and "$n_s$" denote the refractive indexes of auxiliary layer 1 and substrate layer 3, respectively.

Using the above equations (see FIGS. 1A and 1B), an enhanced ellipsometry signal is created by maintaining an auxiliary layer 1 refractive index "n" that is less than or equal to the square root of the product of n, where n is the refractive index of the medium between the light source and sample 2 ($n_o$), times the refractive index of substrate layer 3 ($n_s$), so that the component of the s-polarization of first reflection beam 21 and second reflection beam 22 are out of phase. Using the above equations, auxiliary layer 1 may be tuned by changing thickness (d) and refractive index (n) of auxiliary layer 1 and optimal incident angle (θ) of incident light 19, as required, to produce deconstructive interference about s-polarization, so that the reflectivity of the component with s-polarization, is zero or minimized.

Figure 2A:
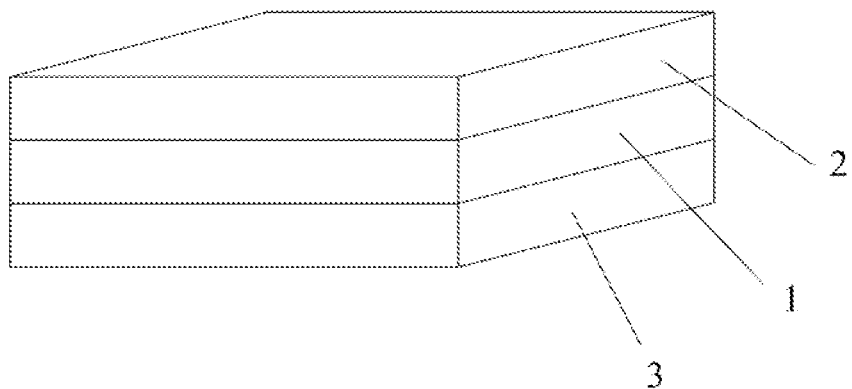
FIG. 2A shows an embodiment of the present invention with one auxiliary layer and one substrate layer.

FIG. 2A shows an exemplary embodiment of the present invention wherein substrate layer 3 is comprised of materials such as silicon or gold and is coated by auxiliary layer 1 comprised of aluminum oxide or silicon oxide. Auxiliary layer 1 is then coated with a sample 2.

Figure 2B:
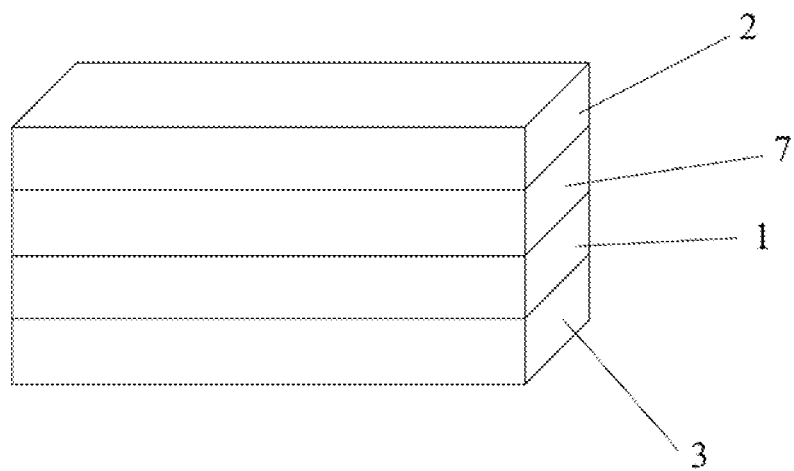
FIG. 2B shows an embodiment of the present invention with one auxiliary layer, one functional layer and one substrate layer.

FIG. 2B shows a second exemplary embodiment of the present invention, which further includes functional layer 7, which can be comprised of a material to protect substrate layer 3 or auxiliary layer 1. Functional layer 7 can also be used as an absorptive surface modifier to enhance the binding or interaction with sample 2, a spectral filter to block out certain frequencies of light, a layer that modifies the Reynolds number of the surface, or silanes to facilitate organic polymer absorption. Thus, there are numerous cited and uncited uses of the functional layer 7, but in all embodiments the functional layer 7 serves a function. The optimal incident angle (θ) and thickness (d) of auxiliary layer 1, made of $SiO_2$ and $Al_2O_3$, for a silicon substrate for various specimen types can be found in the following table:

| Wavenumbers ($cm^{-1}$) | Vibration modes | $SiO_2$ θ (deg) | $SiO_2$ d (nm) | $Al_2O_3$ θ (deg) | $Al_2O_3$ d (nm) |
|---|---|---|---|---|---|
| 3300 | OH, NH str | 70 | 707 | 43 | 485 |
| 3000 | CH str | 70 | 782 | 44 | 538 |
| 2200 | CN, NCO str | 71 | 1096 | 48 | 759 |
| 1700 | C=O str | 72 | 1463 | 51 | 1021 |
| 1300 | C—O str, HCH ben | N/A | Absorptive | 56 | 1409 |
| 800 | C—O, C—C str | N/A | Absorptive | 66 | 2675 |

Figure 3:
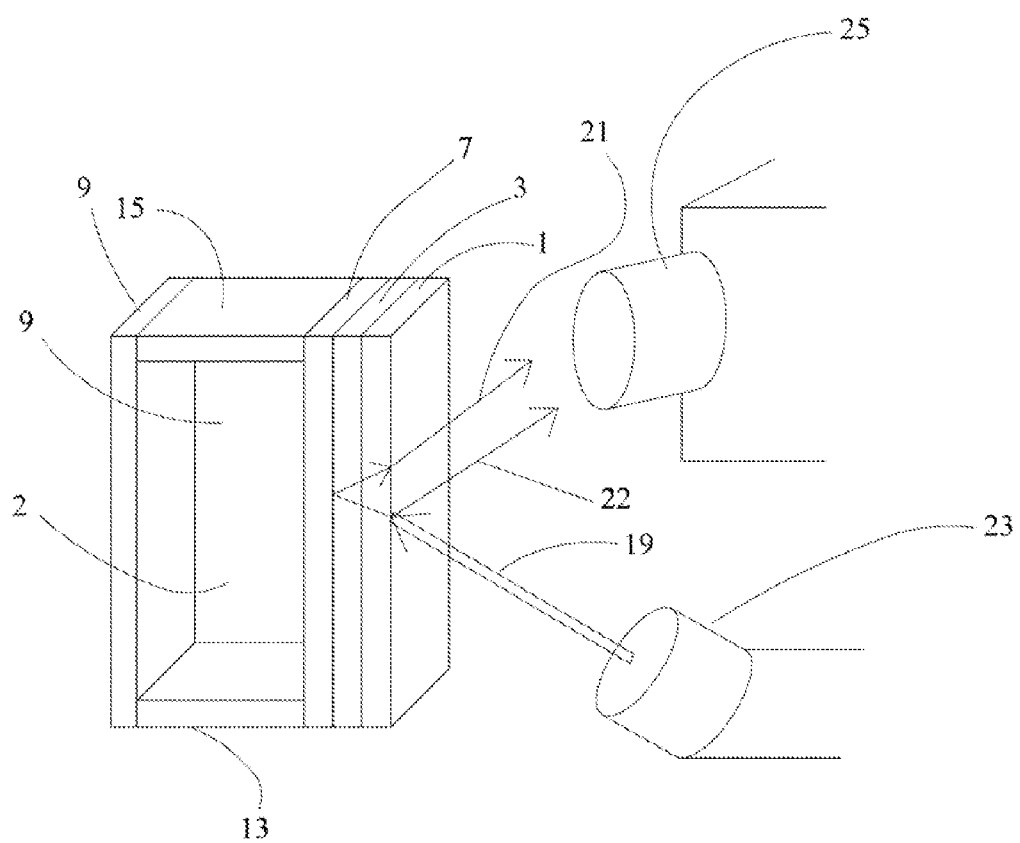
FIG. 3 shows an ellipsometry liquid/gas/flow cell, with the sample placed behind a substrate layer and an auxiliary layer.

FIG. 3 is an exemplary embodiment of an ellipsometry liquid/gas/flow cell with sample 2 located behind substrate layer 3 and auxiliary layer 1, which form the present invention. In this embodiment, substrate layer 3 must be transparent or translucent at the wavelength of interest because sample 2 is within a cell formed by cell walls 9, cell top 15 and cell bottom 13. Cell top 15 and cell bottom 13 may have an opening, if necessary, for example, if the cell is part of a flow-through system such as an HPLC or GLC apparatus. The present invention makes up part of one of the walls of the cell and may further consist of functional layer 7, as shown in FIG. 3, which protects substrate layer 3 or acts as an absorptive or reactive surface. Functional layer 7 is transparent at the desired wavelength.

In the embodiment shown, auxiliary layer 1 is coated on substrate layer 3. Incident light 19, at the desired wavelength, from light source 23 is aimed at auxiliary layer 1 at a prescribed angle. This will produce two out-of-phase reflection beams in their s-polarization components, first reflection beam 21 and second reflection beam 22, which can be detected by detector 25.

Figure 4:
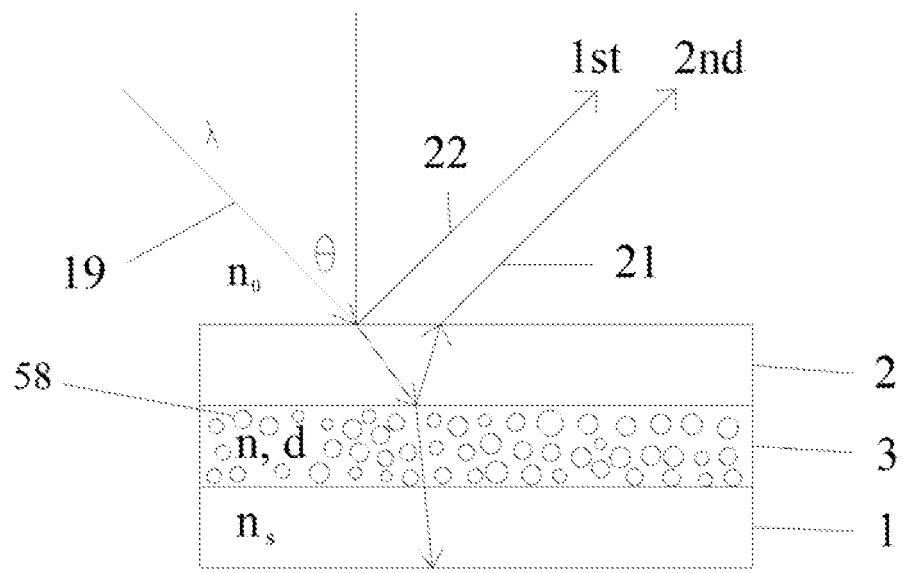
FIG. 4 shows the embodiment in FIG. 1, where the refraction index "n" is tuned by placing nanovoids in the invention's auxiliary layer.

FIG. 4 shows an exemplary embodiment of the present invention which, further includes nanovoids 58. Nanovoids 58 are used to fine-tune the refractive index (n) of materials used for auxiliary layer 1.

The process and the formulation to incorporate nanovoids 58 into solid organic and inorganic materials are being used in the semiconductor industry to produce low dielectric films. (*Dielectric Films for Advanced Microelectronics*, edited by M. Baklanov, M. Green & K. Maex, John Wiley & Sons, Ch. 1, §1.5; Ch. 2, §2.3 (2007) ISBN 10:0-470-01360-5, herein incorporated by reference.)

Based on the Maxwell-Garnett effective medium approximation (Marcelo M. Viana, Tarik D. S. Mohallem, Gabriel L. T. Nascimento, & Nelcy D. S. Mohallem, Nanocrystalline Titanium Oxide Thin Films Prepared by Sol-Gel Process, *Brazilian J. Physics* 36 (3B), 1081 (2006), herein incorporated by reference), the refractive index, $n_{eff}$, of a nanoporous material can be expressed in terms of the refractive index of the dense material, $n_b$, and the porosity, P, defined as the volume fraction occupied by the nanovoids 58.

$$\frac{n_{\text{eff}}^2 - 1}{n_{\text{eff}}^2 + 2} = (1 - P)\frac{n_b^2 - 1}{n_b^2 + 2}$$

Accordingly, the present invention is novel in that it permits one to produce an enhanced signal for a specific sample type for spectroscopic ellipsometry by using an auxiliary layer of a specific thickness and refractive index coated on a substrate layer. The auxiliary layer can be a single layer or it can be comprised of multiple layers as long as it can produce a deconstructive interference about s-polarization. In addition to gold and silicon, the substrate may be glass, metal, oxide, semiconductor, or even absorptive material.

Given the numerous embodiments of the present invention made possible by various combinations of substrates and auxiliary layers and given that the described cell can be flow-through or closed, the scope of the invention should be determined by the appended claims and their legal equivalents, rather than by the examples given.

What is claimed is:

1. An apparatus for enhancing the electromagnetic signal of a sample for ellipsometry comprising:
   a) at least one substrate layer;
   b) at least one auxiliary layer bound to said at least one substrate layer, wherein said at least one auxiliary layer has a thickness and refractive index which produces deconstructive interference about s-polarization reducing the reflection of a component with s-polarization to a minimum,
   wherein said thickness and said refractive index of said at least one auxiliary layer are dictated by the equations $$d = \frac{\lambda}{\sqrt{A(n-1) + B(n-1)^2}} \text{ and } n_{op} = .85 + 0.189 n_s,$$

where $A = 37.26(n_s - 1.682)^{-1/8}$, $B = 14.587(n_s - 2.171)^{1/6.5}$, $n \neq 1$, d is said thickness of said auxiliary layer, $\lambda$ is the wavelength of a light source, n is the refractive index of said auxiliary layer, $n_s$ the refractive index of said substrate layer, and $n_{op}$ is the optimal refractive index.

2. The apparatus of claim 1, wherein a second thickness and a second refractive index of an at least one second auxiliary layer are dictated by the equations $$d' = \left(\frac{\lambda}{4\sqrt{n^2 - n_0^2 \sin^2 \theta}}\right) \text{ and } n' \leq \sqrt{n_0 n_s},$$

where $n'^2 \neq n_0^2 \sin^2 \theta$, d' is said second thickness of said second auxiliary layer $\lambda$ is said wavelength of said light source, n' is said second refractive index of said second auxiliary layer, $n_0$ is said refractive index of a medium between said light source and said sample, $n_s$ said refractive index of said substrate layer, and $\theta$ is an incident angle of said light source.

3. The apparatus of claim 1, wherein said at least one substrate layer is comprised of gold.

4. The apparatus of claim 1, wherein said at least one substrate layer is comprised of silicon.

5. The apparatus of claim 1, wherein said at least one substrate layer is comprised of germanium.

6. The apparatus of claim 1, wherein said at least one substrate layer is comprised of zinc selenide.

7. The apparatus of claim 1, wherein said at least one auxiliary layer is comprised of aluminum oxide.

8. The apparatus of claim 1, wherein said at least one auxiliary layer is comprised of silicon oxide.

9. The apparatus of claim 1, wherein said at least one substrate layer is nonporous organosilicates.

10. The apparatus of claim 1, wherein there are multiple auxiliary layers.

11. The apparatus of claim 1, wherein there are multiple substrate layers.

12. The apparatus of claim 1, wherein said at least one auxiliary layer contains nanovoids that alter the reflective properties of said at least one auxiliary layer.

13. A method for enhancing the electromagnetic signal of a sample for spectroscopic ellipsometry, comprising:
   a) coating a substrate with a material to create at least one auxiliary layer of a specific thickness; and
   b) directing a light source at a given angle to said at least one auxiliary layer, which is bound to said substrate, said at least one auxiliary layer is a thickness that produces deconstructive interference about s-polarization so that the reflectivity of an s-component is reduced,
   wherein said thickness and said refractive index of said at least one auxiliary layer are dictated by the equations $$d = \frac{\lambda}{\sqrt{A(n-1) + B(n-1)^2}} \text{ and } n_{op} = .85 + 0.189 n_s,$$

where $A = 37.26(n_s - 1.682)^{1/8}$, $B = 14.587(n_s - 2.171)^{1/6.5}$, $n \neq 1$, d is said thickness of said auxiliary layer, $\lambda$ is the wavelength of a light source, n is the refractive index of said auxiliary layer, $n_s$ is the refractive index of said substrate layer, and $n_{op}$ is the optimal refractive index; and wherein said a second thickness is dictated by equation $$d' = \left(\frac{\lambda}{4}\right)\sqrt{\frac{n_s^2 - 2n'^2 + 1}{(n'^2 - 1)(n_s^2 - n^2)}}$$

and angle of said light source is directed at said angle is dictated by the equation $$\theta = \tan^{-1}\left(\sqrt{\frac{n_s^2 - n^4}{n^2 - 1}}\right)$$

to produce optimal sensitivity in said spectroscopic ellipsometry where $n^2 \geq 1$ and $n_s^2 > n^2$, d' is said second thickness of said second auxiliary layer, $\lambda$ is the wavelength of the light source, n' is said second refractive index of said second auxiliary layer, $n_0$ is said refractive index of a medium between said light source and said sample, $n_s$ said refractive index of said substrate layer, and $\theta$ is an incident angle of said light source.

14. The method of claim 13, wherein said reflectivity of said s-component is reduced to zero.

15. The method of claim 13, wherein a third thickness and a third refractive index of an at least one third auxiliary layer are dictated by the equations $$d'' = \left(\frac{\lambda}{\sqrt[4]{n^2 - n_0^2 \sin^2\theta}}\right) \text{ and } n'' \leq \sqrt{n_0 n_s}$$

where $n''^2 \neq n_0^{32} \sin^2\theta$, $d''$ is said third thickness of said third auxiliary layer $\lambda$ is said wavelength of said light source, $n''$ is said third refractive index of said third auxiliary layer, $n_0$ is said refractive index of a medium between said light source and said sample, $n_s$ said refractive index of said substrate layer, and $\theta$ is an incident angle of said light source.

16. The method of claim 13, which further includes coating said substrate with at least one additional auxiliary layer.

17. An apparatus for enhancing the ellipsometry signal of a sample in a cell, comprising:
   a) a cell that has all or part of its wall(s) consisting of at least one substrate layer that is transparent to a desired part of the electromagnetic spectrum; and
   b) at least one auxiliary layer bound to said at least one substrate layer, wherein said at least one auxiliary layer is of a specific thickness either alone or in combination with other auxiliary layers with its characteristics dictated by the equations $$d = \frac{\lambda}{\sqrt{A(n-1) + B(n-1)^2}}, \theta = \tan^{-1}\left(\frac{1}{c(n-1) + D(n-1)^2}\right),$$

and $n_{op} = 0.85 + 0.189 n_s$, where $A = 37.26(n_s - 1.682)^{-1/8}$, $B = 14.587(n_s - 2.171)^{1/6.5}$, $C = (-0262 + 0.454 n_s)^{-1}$, and $D = -(1.181 - 0.112 n_s)^4$, wherein $n \neq 1$, d is said thickness of said auxiliary layer, $\lambda$ is the wavelength of a light source, n is the refractive index of said auxiliary layer, $n_s$ the refractive index of said substrate layer, and $n_{op}$ is the optimal refractive index.

18. The apparatus of claim 17 wherein said cell has four cell walls, one of said cell walls, which is made of a substrate.

19. The apparatus of claim 17, wherein said cell is cylindrical.

20. The apparatus of claim 17, wherein said cell may be operatively coupled with a chromatography component.

21. The apparatus of claim 17, wherein said sample is isolated from said at least one substrate layer by a functional layer.

22. The apparatus of claim 17, wherein said cell is sealed by a cell top and a cell bottom, thus forming a closed cell.

23. The apparatus of claim 22, wherein said cell top and said cell bottom are partially open to permit the attachment of piping to the cell to permit the flow of said sample through said cell.

24. The apparatus of claim 22, wherein said cell top and said cell bottom have a means to attach piping to each of them.

* * * * *